United States Patent [19]

Shanzer et al.

[11] Patent Number: 5,101,066
[45] Date of Patent: Mar. 31, 1992

[54] EXTRACTANTS FOR THE SEPARATION OF TRANSITION AND RELATED METAL IONS

[75] Inventors: Abraham Shanzer; Jacqueline Libman; Shneior Lifson, all of Rehovot, Israel

[73] Assignee: Yeda Research and Development Co. Ltd., Rehovot, Israel

[21] Appl. No.: 441,102

[22] Filed: Nov. 24, 1989

[30] Foreign Application Priority Data

Nov. 25, 1988 [IL]  Israel ....................................... 088498

[51] Int. Cl.$^5$ .......................................... C07C 229/00
[52] U.S. Cl. ....................................... 560/169; 75/722; 560/41; 562/621; 562/622; 562/623
[58] Field of Search ..................... 560/169, 170, 41; 562/623, 621, 622

[56] References Cited

U.S. PATENT DOCUMENTS

| | | | |
|---|---|---|---|
| 4,083,996 | 4/1978 | Tanaka | 562/623 |
| 4,256,765 | 3/1981 | Munakata | 562/623 |
| 4,604,407 | 8/1986 | Haslanger | 562/621 |
| 4,939,299 | 7/1990 | Coleman | 562/623 |
| 4,966,997 | 10/1990 | Shanzer | 562/623 |

*Primary Examiner*—Michael L. Shippen
*Attorney, Agent, or Firm*—Browdy and Neimark

[57] ABSTRACT

There are provided novel compounds useful as selective extractants of metal values from aqueous systems comprising a plurality of such ionic species. There is further provided a process for the production of the novel compounds. The invention also relates to a process of selective metal extraction by means of the novel compounds of the invention.

11 Claims, 1 Drawing Sheet

EXTRACTANTS FOR THE SEPARATION OF TRANSITION AND RELATED METAL IONS

FIELD OF THE INVENTION

The invention relates to a novel group of metal extractants. The invention further relates to the production of these and to a process of selective metal extraction by means of such extracting agents. Furthermore the invention relates to metal values, whenever obtained by a process involving the use of the novel extractants.

BACKGROUND OF THE INVENTION

Separation, purification and analysis of metal ions is of great importance in many diverse areas. Examples are hydrometallurgy and electroplating processes, metal recovery and waste treatment, the preparation of high purity materials for the electronic and laser industry and the analysis of trace metals in body fluids. Two of the methods that are inherently applicable to most of these fields are solvent extraction[1] and membrane technologies[2]. Solvent extraction has extensively been applied for the separation of metal ions in bulk quantities in hydrometallurgic processes. Over the years, much emphasis has been placed on improving the performance of a very small number of simple ligands by carefully modifying extraction conditions such as pH, masking agents, stripping agents and the nature of the organic solvent. Only marginal efforts have been devoted to the design of tailor-made ligands that would extract a specific metal ion in the presence of a plurality of other[3-6]. The object of the present invention is to provide binders that selectively extract a specific metal ion from a mixture of many cations by forming stable complexes of 1:1 stoichiometry. an example is a tetradentate ligand that separates quantitatively $Cu^{2+}$ from a mixture of six bivalent transition and related metal ions.

SUMMARY OF THE INVENTION

The invention relates to a novel group of metal extractants. The invention further relates to the production of these and to a process of selective metal extraction by means of such extracting agents. Furthermore the invention relates to metal values, whenever obtained by a process involving the use of the novel extractants. More specifically, the invention relates to novel compounds of the general formula:

$$R^2R^3C-[CH_2-O-(CH_2-)_n-CO-[NHCHR(CH_2)_mCO]_q-NOHR^1]_2$$

wherein
 n designates 1 or 2,
 m designates 0, 1 or 2,
 q designates 0 or 1,
 R, $R^1$, $R^2$ and $R^3$ independently designate each H, alkyl, aryl, aralkyl, alkyl—$COOR^1$, alkyl—$CONHR^1$ or alkyl—$CONR_2$, where $R^1$ designates alkyl.

DETAILED DESCRIPTION OF EMBODIMENTS

Figure 1:
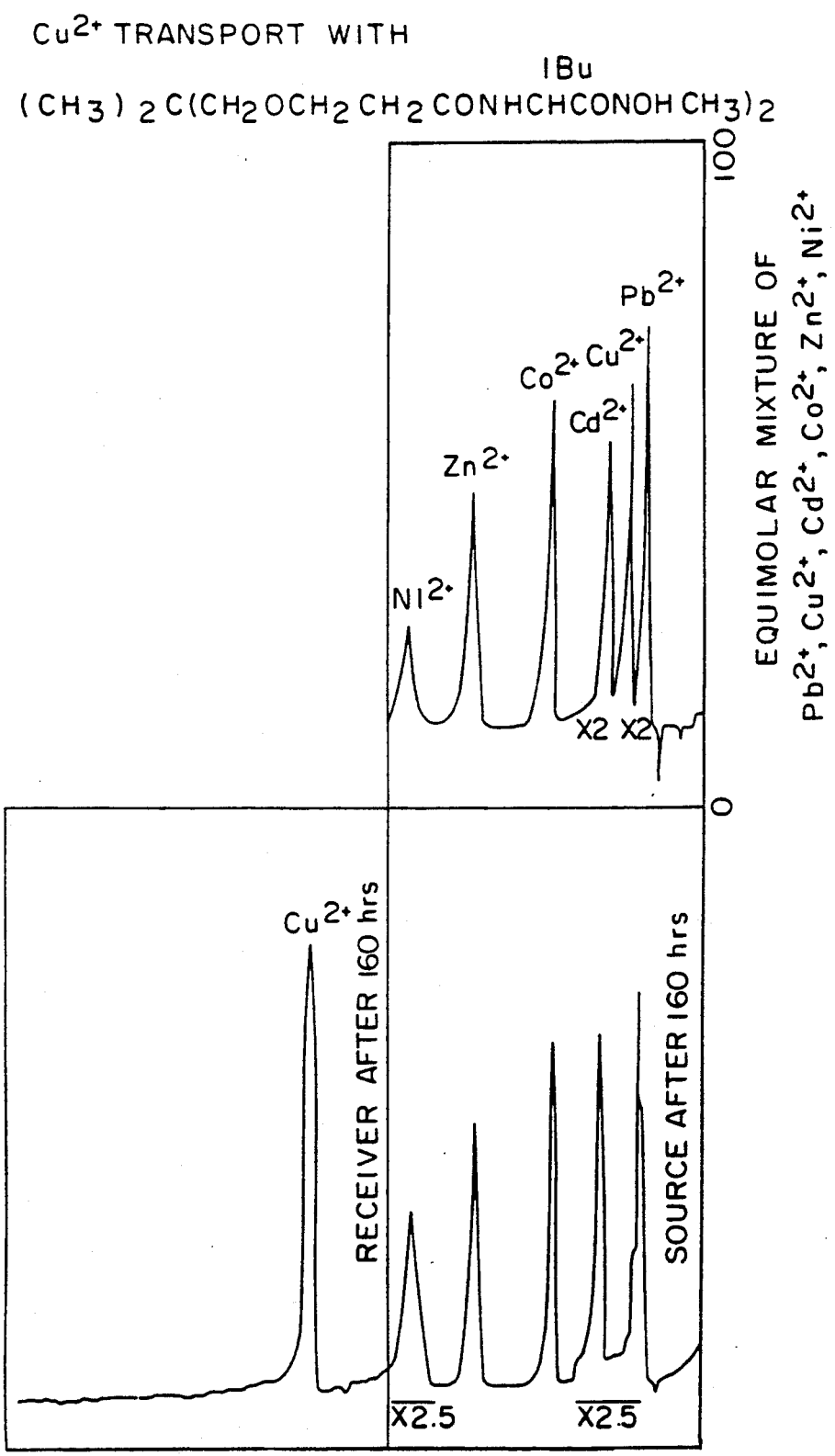
FIG. 1 shows ion chromatographic analysis performed in a DIONEX instrument of water containing equimolar mixture of cations $Pb^{2+}$, $Cu^{2+}$, $Cd^{2+}$, $Co^{2+}$, $Zn^{2+}$, $Ni^{2+}$ (top right); receiver arm containing only $Cu^{2+}$ extracted after 160 hours using compound of the invention wherein n=2, m=0, q=1, R=iBu, $R^1=R^2=R^3=CH_3$ (bottom left) and original mixture after 160 hours extraction (bottom right).

Preferred compounds are those wherein R, $R^1$, $R^2$ and $R^3$ designate lower alkyl with n=1 or 2, m=0, and q=0 or 1. Amongst other preferred compounds, are those with n=1 or 2, q=zero or 1, $R^1$=lower alkyl, preferably methyl, or —$CH_2CH_2COOAlk$, where Alk designates lower alkyl, with $R^2$=methyl and $R^3$=methyl or propyl.

The compounds of the present invention are tetradentate ligands which are suited for the selective extraction of a certain cation from a mixture of cations.

The binders of the invention are designed in a modular fashion and fulfil the following requirements: i) they define an ion binding cavity to fit a specific metal ion, and preferably (ii) create a lipophilic envelope. The cavity comprises two hydroxamate groups as binding sites. These groups are organized by the molecules' skeleton to form tetrahedral cavities of appropriate size. The lipophilic envelope is created by the use of lipophilic side chains to attain a solubility of the molecule and of its complex in lipid membranes.

Hydroxamate groups were chosen as ion binding groups in view of three major considerations: (i) their high binding affinity to a large range of metal ions, (ii) their pH dependent binding properties that allow to control metal uptake on one side of the membrane and metal release on the other side, and (iii) their capability to form electrically neutral complexes when binding divalent transition metal ions thereby enhancing solubility in lipids.

According to this general principle, ion binders and carriers were designed and synthesized in a modular fashion. The planned modularity simplifies synthesis on one hand, and allows variability in the assembly of the modules on the other.

The synthesis of these binders was performed in essentially three steps as illustrated beneath for the family of compounds with n=2, m=O, q=1.

(i) Alkylation of the parent alcohol and transformation to the corresponding acid derivative,

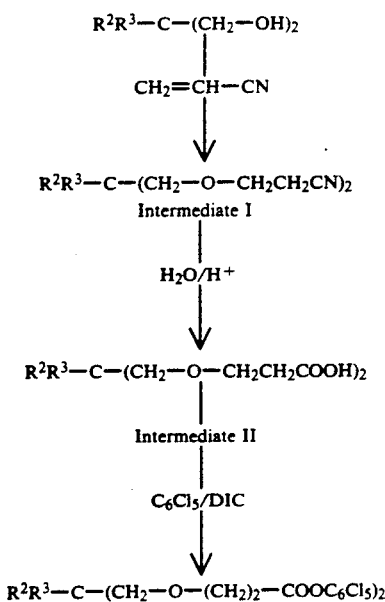

-continued
Intermediate III

DIC = Diisopropylcarbodiimide (ii) Preparation of the amino-hydroxamate residues by condensation of the chosen amino acid with hydroxyl amine. This involves preparation of the pentachlorophenolate IV, coupling with hydroxylamine to give V and removal of the protecting group by hydrogenation to give VI.

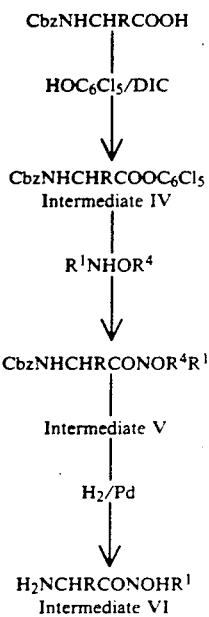

where $Cb_2$ is carbobenzoxy, (iii) Condensation of the acid derivative with the desired amino-hydrozamate to the final products:

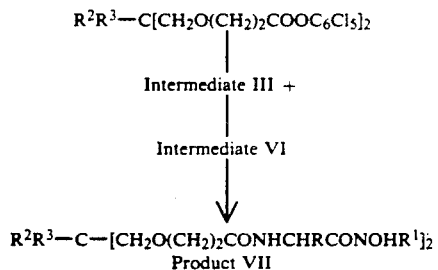

According to this procedure compounds were prepared where n=2, m=O, q=1 $R^1=R^2=R^3=$Me and R=iBu, and where n=2, q=0, $R^1=R^2=R^3=$Me.

In a related sequence compounds were prepared where n=1, m=O and q=1. The steps are as follows:

(i) Alkylation of the parent alcohol and transformation to the corresponding acid derivative,

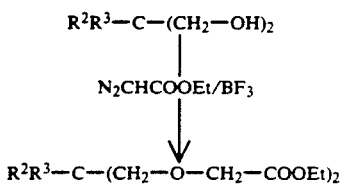

-continued
Intermediate VIII

1. $H_2O/OH^-$
2. $HO-C_6Cl_5/DIC$ $R^2R^3-C-(CH_2-O-CH_2-COOC_6Cl_5)_2$ Intermediate IX (ii) Preparation of the amino-hydroxamate residues by condensation of the chosen amino acid the hydroxyl amine. This involves preparation of the active ester IV, condensation with hydroxylamine to give V, and removal fo the protecting group to give VI.

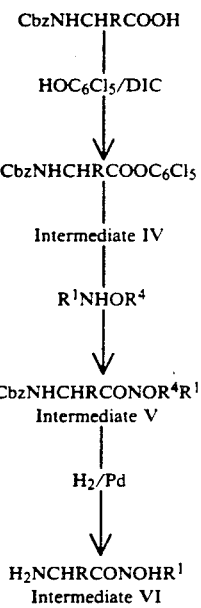

Cbz = Carbobenzoxy (iii) Condensation of the acid derivative with the desired amino-hydroxamate to the final products.

In this manner compounds $R^1=R^2=R^3=$Me, and R=iBu or Me were prepared.

R = iBu, Me

By sequences analogous to those shown above, compounds were prepared where n=1, q=0, $R^1=$Me or $CH_2CH_2COOEt$, $R^2=R^3=$Me or $R^2=$Me and $R^3=$Pr.

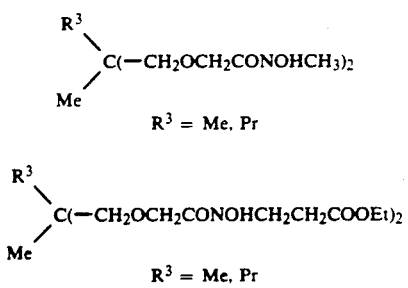

$R^3 = Me, Pr$ $R^3 = Me, Pr$

3. Experimental Procedure of Synthesis of Bishydroxamate VII (n=2, m=O, q=1, R=iBu, $R^1=R^2=R^3=CH_3$)

3.1. Preparation of Biscarboxylate III 9.36 g 1,1,1-tris(hydroxymethyl)propane with 0.6 ml 40% aq. NaOH and then 13.2 ml acrylonitrile (freshly purified by passing through neutral alumina) are added so that the temperature does no exceed 30° C. Then the mixture is stirred overnight at room temperature, neutralized with diluted aq. HCl, dissolved in 500 ml ethyl acetate, washed with water, dried and concentrated to give 18.45 g material (TLC: toluene-ethyl acetate 85-15). The crude product is hydrolyzed by treating 2.40 g with 2.7 ml conc. HCl in an oil bath of 95°-100° C. for 6 hrs. After cooling to room temperature the residue is suspended in ethylacetate, washed with water, dried and concentrated to give 2.1 g diacid. 3.7 g (0.015 mol) of crude diacid are dissolved in 200 ml acetonitrile (dried over alumina), 8.7 g pentachlorophenol and 400 mg dimethylaminopyridine are added, the mixture cooled in an ice bath and treated with 5.0 ml diisopropylcarbodiimide. Then the mixture is allowed to warm up to room temperature and stirred for 1-2 days. Concentration in vacuo and chromatography on silica gel (toluene-ethyl aceytate 98-2) yields 2.83 g of the biscarboxylate III, mp 88°-90° C.

3.2. Preparation of Hydroxamate VI (R=iBu, $R^1=CH_3$)

5.3 g (0.02 mol) Cbz-L-leucine are dissolved in 150 ml acetonitrile (dried over basic alumina), 5.8 g (0.022 mol) pentachlorophenol are added and under cooling 3.9 ml (0.025 mol) diisopropylcarbodiimide. The mixture is stirred for 1 day at room temperature, concentrated, chromatographed on silica gel and then filtered through neutral alumina to provide 10.41 g of pure pentachlorophenolate, mp 125°-126° C. 5.2 g (0.01 mol) of phenolate are dissolved in 50 ml dry methylenechloride and treated with a solution containing 1.04 g (0.0125 mol) methylhydroxyl amine hydrochloride, 1.21 g (0.0125 mol) triethyl amine and 50 mg N-hydroxysuccinimide in 100 ml methylenechloride. The mixture is stirred over night, concentrated in vacuo and the residue chromatographed on silica gel (chloroform-methanol 99-1) to provide 1.30 g pure Z-leuhydroxamate, mp 71°-73° C. 960 mg (0.003 mol) of the latter are dissolved in 100 ml ethanol and hydrogenated at atmospheric pressure in the presence of 500 mg Pd/C, 10%. Filtration, concentration and chromathography on silicagel (chloroform-methanol 8-2) yields 472 mg of pure hydroxamate VI.

3.3. Preparation of Hydroxamate VII (n=2, m=O, q=1, R=iBu), $R^1=R^2=R^3=CH_3$).

1.13 g biscarboxylate III are dissolved in 50 ml dry methylene chloride and treated with a solution containing 675 mg hydroxamate VI, 50 mg N-hydroxysuccinimide and 300 mg imidazole in 50 ml methyleneochloride for 4 days. Chromatography of the crude reaction product on silica gel (chloroform, chloroformmethanol 99-1 as eluents) yields 542 mg of the bishydroxamate VII (mp. 44°-46° C.).

4. Uses of Ion Binders and Carriers

4.1. Selective Metal Extraction and Transport

Several of the ion binders, when incorporated into bulk membranes, selectively extract and transport a specific metal ion from a plurality of cations. An example is the quantitative separation of $Cu^{2+}$ from a mixture of six two-valent metal ions. This is illustrated by the quantitative removal of $Cu^{2+}$ from an equimolar mixture (10 mM each) of $Pb^{2+}$, $Cu^{2+}$, $Cd^{2+}$, $Co^{2+}$, $Zn^{2+}$ and $Ni^{2+}$ in water. Using a bulk membrane consisting of 0.3 mM of the most lipophilic carrier (n=2, m=O, q=1, R=iBu, $R^1=R^2=R^3=CH_3$) in $CHCl_3$ and a receiver containing 0.1M $H_2SO_4$, $Cu^{2+}$ was quantitatively removed without a trace of contamination by other metals (as determined by ion chromatographic analysis on a DIONEX instrument (see FIG. 1). (The experiments were performed in U-Tubes which are the standard laboratroy method for simulating extraction procedures.)

A second example is the removal of $Zn^{2+}$ without any contamination of $Cd^{2+}$ (according to Ion Chromatography) from an equimolar mixture of $Zn^{2+}$ and $Cd^{2+}$ (20 mM each), when applying the same carrier (n=2, m=O, q=1, R=iBu, $R^1=R^2=R^3=CH_3$) at 3.0 mM concentration in chloroform.

A third example is the removal of $Cu^{2+}$ from an equimolar mixture of $Cu^{2+}$ and $Fe^{3+}$ (3 mM each in the presence of 6 mM citric acid titrated to pH 6.8 with KOH) with less than 10% contamination of $Fe^{3+}$, by using a carrier (n=2, m=O, q=0, $R^1=CH_3$) 4.5 mM concentration in chloroform and in the receiver phase 3 mM DTPA at pH2.

Characteristics of some of the carriers prepared:

| n | R | $R^1$ | $R^2$ | $R^3$ | MP | Partition Coefficients |
|---|---|---|---|---|---|---|
| q = 0 | | | | | | |
| 1 | | Me | Me | Me | 142-145 | 2.25 |
| 1 | | Me | Me | Pr | 102-104 | 1.95 |
| 1 | | $CH_2CH_2COOEt$ | Me | Me | oil | 3.16 |
| 1 | | $CH_2CH_2COOEt$ | Me | Pr | oil | |
| 2 | | Me | Me | Me | oil | 0.82 |
| q = 1 | | | | | | |
| 1 | Me | Me | Me | Me | 32-35° C. | 1.95 |
| 1 | iBu | Me | Me | Me | 28-30° C. | 3.7 |
| 2 | iBu | Me | Me | Me | 44-46° C. | 15.8 |

Partition coefficients relate to octanol saline (1:1) partition

BIBLIOGRAPHY

1. A. K. De, S. M. Khopar, R. A. Chalmers, 'Solvent Extraction of Metals', Van Nostrand Reinhold Company, London, 1970.
2. R. W. Baker, M. E. Tuttle, D. J. Kelly and H. K. Lonsdale, J. Membr. Sc., 2, 213 (1977).

3. E. Kimura, C. A. Dalimunte, A. Yamashita, R. Machida, J. Chem. Soc., Chem Comm., 1041 (1985).
4. K. Maruyama, H. Tsukube, T. Araki, J. Chem. Soc., Dalton, 1486 (1981).
5. K. Maruyama, H. Tsukube, T. Araki, J. Amer. Chem. Soc., 102, 3246 (1980).
6. S. Matsuno, A. Ohki, M. Takagi, K. Ueno, Chem. Letters, 1543 (1981).

We claim:

1. A compound of the general formula:

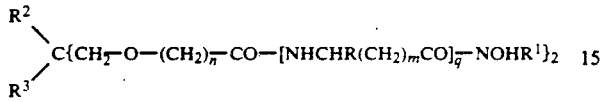

wherein n is 1 or 2; m is zero, 1 or 2; q is zero, 1 or 2; R, $R^1$, $R^2$ and $R^3$ are independently selected from the group consisting of H, alkyl, aryl, aralkyl, alkyl—COOR', alkyl—CONHR' and alkyl—CONR'$_2$ wherein R' is alkyl.

2. A compound according to claim 1, wherein $R^1 = R^2 = R^3 = $—CH$_3$ and R is isobutyl.

3. A compound according to claim 1, wherein n=1, m=0, and q=1, where in $R^1$, $R^2$, $R^3$ are selected from lower alkyl, and R is selected from methyl, ethyl and isobutyl.

4. A compound according to claim 1, wherein n is 1 or 2, q=0, $R^1$ is —CH$_3$ or —CH$_2$CH$_2$COO—Alk, where Alk is lower alkyl, $R^2$ and $R^3$ are lower alkyl.

5. A compound of the formula:

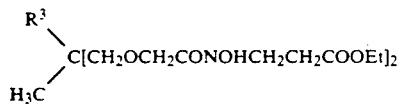

wherein $R^3$ is selected from the group consisting of methyl and propyl.

6. A compound of the formula:

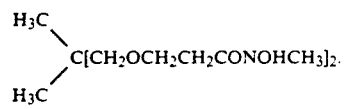

7. A compound of the formula:

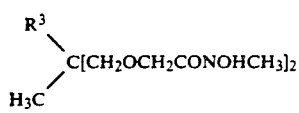

wherein $R^3$ is selected from the group consisting of methyl and propyl.

8. A compound of the formula:

wherein R is selected from the group consisting of methyl and isobutyl.

9. A compound of the formula:

10. A compound according to claim 3 wherein $R^1$, $R^2$ and $R^3$ are each methyl.

11. A compound in accordance with claim 4 wherein $R^2$ and $R^3$ are each methyl.

* * * * *